United States Patent [19]  [11] 4,191,776
Nickl et al. [45] Mar. 4, 1980

[54] BIPHENYL DERIVATIVES

[75] Inventors: Josef Nickl; Erich Muller, both of Biberach/Riss; Berthold Narr, Mettenberg; Walter Haarmann, Biberach/Riss; Wolfgang Schroter, Biberach/Riss; Rudolf Kadatz, Biberach/Riss, all of Fed. Rep. of Germany

[73] Assignee: Boehringer Ingelheim GmbH, Ingelheim am Rhein, Fed. Rep. of Germany

[21] Appl. No.: 852,714

[22] Filed: Nov. 18, 1977

Related U.S. Application Data

[63] Continuation-in-part of Ser. No. 711,953, Aug. 5, 1976, abandoned, which is a continuation-in-part of Ser. No. 577,169, May 14, 1975, Pat. No. 3,993,683.

[51] Int. Cl.$^2$ ............... C07C 147/107; C07C 147/14; A61K 31/44; A61K 31/235
[52] U.S. Cl. .................. 424/308; 260/465 D; 546/294; 560/11; 424/263; 424/304; 424/317
[58] Field of Search .............. 260/516, 470; 560/11; 424/308

[56] References Cited

U.S. PATENT DOCUMENTS 3,549,690 12/1970 Leigh .................................. 260/516
3,549,691 12/1970 Leigh .................................. 260/516

FOREIGN PATENT DOCUMENTS 1121722 7/1968 United Kingdom ............. 260/470

OTHER PUBLICATIONS

Janczewski, Chem. Abst., 66:37570(z) (1967).
Janczewski, Chem. Abst., 69:51794(a) (1968).
Janczewski, Chem. Abst., 68:49239(c) (1968).
Janczewski, Chem. Abst., 81:63036(j) (1974).

Primary Examiner—Bernard Helfin
Assistant Examiner—Michael Shippen
Attorney, Agent, or Firm—Walter G. Weissenberger

[57] ABSTRACT

Compounds of the formula

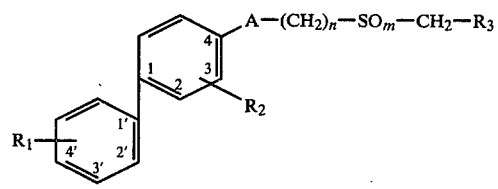

wherein
  $R_1$ is hydrogen, fluorine, chlorine, bromine, methyl, methoxy, methylthio or cyano;
  $R_2$ is hydrogen or fluorine;
  $R_3$ is carboxyl, (alkoxy of 1 to 6 carbon atoms)-carbonyl, methoxy-(alkoxy of 1 to 6 carbon atoms)-carbonyl, (alkenyloxy of 2 to 6 carbon atoms)-carbonyl, (aralkoxy of 7 to 12 carbon atoms)-carbonyl, phenoxy-carbonyl or pyridyl-methoxy-carbonyl,
  A is (alkyl of 1 to 3 carbon atoms)-methylene,
  m is 1 or 2; and
  n is 0, 1, 2 or 3;

and, when $R_3$ is carboxyl, non-toxic salts thereof formed with an inorganic or organic base. The compounds as well as the salts are useful as antithrombotics, anticholesteremics and anticoagulants.

5 Claims, No Drawings

BIPHENYL DERIVATIVES

This is a continuation-in-part of copending application Ser. No. 711,953 filed Aug. 5, 1976, now abandoned which in turn is a continuation-in-part of application Ser. No. 577,169 filed May 14, 1975, now U.S. Pat. No. 3,993,683.

The invention relates to novel derivatives of biphenyl and salts thereof, as well as to various methods of preparing these compounds.

More particularly, the present invention relates to a novel class of biphenyl derivatives represented by the formula

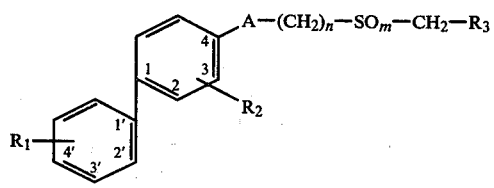

wherein $R_1$ is hydrogen, fluorine, chlorine, bromine, methyl, methoxy, methylthio or cyano;

$R_2$ is hydrogen or fluorine;

$R_3$ is carboxyl, (alkoxy of 1 to 6 carbon atoms)-carbonyl, methoxy-(alkoxy of 1 to 6 carbon atoms)-carbonyl, (alkenyloxy of 2 to 6 carbon atoms)-carbonyl, (aralkoxy of 7 to 12 carbon atoms)-carbonyl, phenoxy-carbonyl or pyridylmethoxy-carbonyl;

A is (alkyl of 1 to 3 carbon atoms)-methylene;

m is 1 or 2; and n is 0, 1, 2 or 3;

diastereoisomers thereof, optically active antipodes thereof, and, when $R_3$ is carboxyl, non-toxic salts thereof formed with an inorganic or organic base.

Especially preferred embodiments of $R_3$ are methoxycarbonyl, ethoxycarbonyl, (2-methoxy-ethoxy)-carbonyl, n-propoxy-carbonyl, isopropoxy-carbonyl, n-butoxy-carbonyl, isobutoxy-carbonyl, n-pentyloxy-carbonyl, isoamyloxy-carbonyl, hexyloxy-carbonyl, benzyloxy-carbonyl, allyloxy-carbonyl and crotyloxy-carbonyl.

The compounds embraced by formula I above may be prepared by the following methods:

Method A

For the preparation of a compound of the formula I, wherein $R_1$ is other than methylthio when m is 2, by oxidation of a thioether of the formula

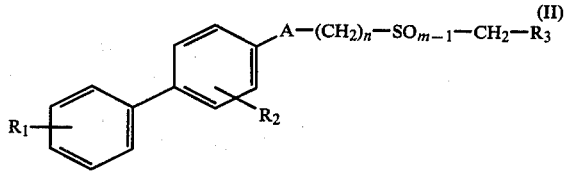

wherein $R_1$, $R_2$ $R_3$, A, m and n have the meanings defined above.

The oxidation is preferably carried out in the presence of a solvent, such as in water, water/pyridine, acetone, glacial acetic acid, dilute sulfuric acid or trifluoroacetic acid, depending on the particular oxidizing agent which is used, and advantageously at temperatures between $-80°$ and $100°$ C.

For the preparation of a compound of the formula I wherein m is 1, the oxidation is advantageously effected with an equimolar quantity of a suitable oxidizing agent, such as with hydrogen peroxide in glacial acetic acid at 0° to 20° C., or in acetone at 0° to 60° C.; with a peracid, such as performic acid in glacial acetic acid or trifluoroacetic acid at 0° to 50° C.; with sodium metaperiodate in equeous methanol or ethanol at 15° to 25° C.; with tert. butyl hypochlorite in methanol at $-80°$ to $-30°$ C.; with iodobenzene dichloride in aqueous pyridine at 0° to 5° C.; with nitric acid in glacial acetic acid at 0° to 20° C.; with chromic acid in glacial acetic acid or in acetone at 0° to 20° C.; and with sulfuryl chloride in methylene chloride at $-70°$ C. The thioether-chloro-complex thus obtained is then hydrolyzed with aqueous ethanol.

For the preparation of a compound of the formula I, wherein m is 2, the oxidation is effected with one or with two mol equivalents of a suitable oxidizing agent, such as with hydrogen peroxide in glacial acetic acid at 20° to 100° C. or in acetone at 0° to 60° C.; with a peracid, such as performic acid or m-chloroperbenzoic acid, in glacial acetic acid, trifluoroacetic acid or chloroform at temperatures between 0° and 50° C.; with nitric acid in glacial acetic acid at 0° to 20° C.; with chromic acid or potassium permanganate in glacial acetic acid, water/sulfuric acid or acetone at 0° to 20° C. Thus, if in a compound of the formula II m is 1, the reaction is preferably carried out with 2 molar equivalents of the particular oxidizing agent, and if m is 2, analogously with one equivalent.

Method B

For the preparation of a compound of the formula I, wherein $R_3$ is other than carboxyl, by reacting a compound of the formula

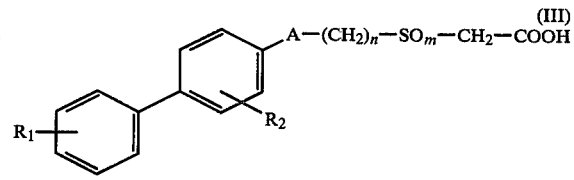

wherein $R_1$, $R_2$, A, n and m have the meanings previously defined, or a halide or anhydride thereof, with a compound of the formula $$R_3'—X \qquad (IV)$$

wherein $R_3'$ has the same meaning as $R_3$ except carboxyl, and X is hydroxyl, chlorine, bromine, iodine, sulfonyl or phosphoryl or diazo.

The reaction is carried out in the presence of a solvent, such as ether, chloroform, benzene, tetrahydrofuran, dioxane, dimethyl sulfoxide, dimethylformamide, hexamethylphosphoric acid-triamide, or in the presence of an excess of the compound of the formula IV, and optionally in the presence of an acid-activating and/or dehydrating agent and optionally in the presence of a base, at temperatures between $-20°$ and 150° C.

If compound IV is a carbinol, such as methanol, ethanol, propanol, isoamylalcohol, n-hexanol, 2-methoxyethanol, allyl alcohol, phenol or benzyl alcohol, the reaction is carried out in the presence of an acid, such as sulfuric acid, p-toluene-sulfonic acid or hydrogen chloride; or an acid-activating agent such as phosphorus oxychloride, thionyl chloride or chlorosulfonic acid; or a dehydrating agent, such as cyclohexylcarbodiimide, carbonyldiimidazole or 2,2-dimethoxypropane; or with a corresponding chloroformate, optionally in the presence of a base, such as potassium carbonate or triethylamine; and preferably at temperature between 20° and 100° C.

If compound IV is a sulfate, such as dimethyl sulfate; or a phosphate, such as triethylphosphate; or a halide, such as methyl iodide, ethyl iodide or allyl bromide, the reaction is carried out in a dipolar aprotic solvent in the presence of a base, such as potassium carbonate, calcium hydroxide or sodium hydroxide, and preferably at temperatures between 20° and 80° C. The reaction may, however, also be carried out under the conditions of a phase transfer-catalyzed 2-phase reaction, for example between chloroform and water, in the presence of a quaternary ammonium salt, such as terabutyl ammonium iodide.

The end products obtained pursuant to methods A and B may, if desired, be separated into their optically active antipodes by conventional methods, such as by chromatography on an optically active carrier or by fractional crystallization of their salts formed with optically active bases.

If the end product obtained by any of the above described methods is one of the formula I wherein $R_3$ is a carboxylic ester group, the same may, if desired, be converted into the corresponding free carboxylic acid by hydrolysis.

Those compounds of the formula I wherein $R_3$ is free carboxyl may, if desired, be converted into non-toxic, pharmacologically acceptable salts thereof formed with inorganic or organic bases. Examples of such salts are those formed with sodium hydroxide, potassium hydroxide, cyclohexylamine or the like.

The starting compounds of the formulas II to IV may be prepared by methods described in the literature, as illustrated in Examples A to G below.

The following examples illustrate the present invention and will enable others skilled in the art to understand it more completely. It should be understood, however, that the invention is not limited solely to the particular examples given below.

Preliminary remarks:

(1) The following commercially available carriers were used for thin-layer chromatography:
Carrier 1=Polygram ® SIL G/UV$^{254}$, manufactured by Macherey, Nagel & Co.
Carrier 2=Silicagel—preprepared plates 60 F—254, manufactured by E. Merck (2) The following solvents were used:
Tetrahydrofuran dried over potassium hydroxide, or dimethyl sulfoxide dried over a molecular sieve (4 AE).

(3) For column chromatography, silicagel manufactured by ICN-Woelm, Eschwege, Germany (grain size: 0.063–0.2 mm) was used.

Preparation of starting compounds:

EXAMPLE A

[1-(2'-Fluoro-4-biphenylyl)-ethylthio]-acetic acid 6.35 gm (0.055 mol) of 80% mercaptoacetic acid were admixed in 70 ml of methanol with a solution of 6.2 gm (0.11 mol) of potassium hydroxide in 6.2 ml of water. To the solution of dipotassium salt, 11.7 gm (0.05 mol) of 1-(2'-fluoro-4-biphenylyl)-1-chloro-ethane were added, the reaction mixture was rinsed with 20 ml of methanol and stirred for 18 hours at room temperature. Subsequently, the mixture was evaporated, the residue was digested with acetone, and the precipitated potassium salt was suction-filtered off. The free acid was obtained by dissolving the salt in water and acidifying the solution. M.p 128°–130° C. (from toluene). Yield: 55% of theory.

EXAMPLE B

[1-(2'-Fluoro-4-biphenylyl)-propylthio]-acetic acidmethyl ester 101.5 gm (0.905 mol) of potassium tert. butylate, suspended in 500 ml of dimethylformamide, were admixed, while stirring and cooling under exclusion of air, with 96.0 gm (0.905 mol) of thioglycolic acid methyl ester. To the solution of the potassium salt, the mixture was admixed with 205.9 gm (0.822 mol) of 1-chloro-1-(2'-fluoro-4-biphenylyl)propane [prepared by reduction of 2'-fluoro-4-biphenylylethylketone with sodium borohydride and subsequent reaction of the obtained 1-hydroxy-1-(2'-fluoro-4-biphenylyl)-propane with hydrochloric acid in benzene], and the mixture was stirred for 4 hours at room temperature. Subsequently, 2 liters of water were added, and the reaction product was isolated by extraction with ethyl acetate, and washing, drying and evaporating of the extract. Yield: 254 gm (97% of theory); oil, $R_f$-value: 0.5 (cyclohexane-ethyl acetate=9:1 on silicagel-polygram-plates).

The following starting compounds were prepared in analogous manner:

(4-Biphenylyl-methylthio)-acetic acid methyl ester; oil, $R_f$-value: 0.6 (cyclohexane-ethyl acetate=4:1 on silicagel-polygram-plates)

[2-(4-Biphenylyl)-ethylthio]-acetic acid methyl ester; oil, $R_f$-value: 0.5 (cyclohexane-ethyl acetate=4:1 on silicagel-polygram-plates)

[1-(4-Biphenylyl)-ethylthio]-acetic acid methyl ester; oil, $R_f$-value: 0.6 (cyclohexane-ethyl acetate=4:1 on silicagel-polygram-plates)

[1-(2'-Fluoro-4-biphenylyl)-ethylthio]-acetic acid methyl ester; oil, $R_f$-value: 0.6 (cyclohexane-ethyl acetate=4:1 on silicagel-polygram-plates)

[2-(2'-Fluoro-4-biphenylyl)-propylthio]-acetic acid methyl ester; oil, $R_f$-value: 0.6 (cyclohexane-ethyl acetate=4:1 on silicagel-polygram-plates)

[3-(4-Biphenylyl)-butylthio]-acetic acid methyl ester; oil, $R_f$-value: 0.5 (cyclohexane-ethyl acetate=4:1 on silicagel-polygram-plates)

[3-(2'Fluoro-4-biphenylyl)-butylthio]-acetic acid methyl ester; oil, $R_f$-value: 0.5 (cyclohexane-ethyl acetate=4:1 on silicagel-polygram plates)

EXAMPLE C

[1-(2'-Fluoro-4-biphenylyl)-propylthio]-acetic acid 220 gm of the methyl ester obtained in Example B were hydrolized with 58.2 gm of potassium hydroxide in 900 ml of ethanol by boiling for one hour. Subsequently, the mixture was diluted with 1800 ml of water, the neutral components were extracted with ether, and the free acid was precipitated from the alkaline phase. By extraction with ether, and washing, drying and evaporating the ethereal extract, the reaction product was isolated. Yield: 130 gm (62% of theory); oil, $R_f$-value: 0.7 (cyclohexane-ethyl acetate=1:1 on silicagel-polygram-plates).

The following compounds were prepared in analogous manner:

[1-(2'-Fluoro-4-biphenylyl)-ethylthio]-acetic acid; m.p. 125°–127° C. (from benzene-cyclohexane=2:1)

[2-(2'-Fluoro-4-biphenylyl)-propylthio]-acetic acid; oil, $R_f$-value: 0.35 (benzene/ethyl acetate/methanol=8:4:2 on preprepared silicagel plates).

EXAMPLE D

[1-(2'Fluoro-4-biphenylyl)-ethylthio]-acetic acid 50 gm (0.23 mol) of 1-(2'-fluoro-4-biphenylyl)-1-hydroxy-ethane, m.p. 88° C., (prepared from 2'-fluoro-4-biphenylyl-methyl-ketone by reduction with sodium borohydride in methanol) were dissolved in 500 ml of benzene, 32.2 gm (0.276 mol) of 80% mercapto-acetic acid and 1 gm of p-toluenesulfonic acid were added, and the mixture was heated at its boiling point for 1 hour, using an apparatus equipped with a water trap. 20.5 ml of water were separated. The benzene solution was washed with water after cooling, dried and evaporated. The crystalline residue was recrystallized from benzene/cyclohexane (2:1), whereby 38.0 gm (61.5% of theory) of the title compound, m.p. 125°–127° C., were obtained.

EXAMPLE E

[1-(2'Chloro-4-biphenylyl)-ethylthio]-acetic acid

1. [1-(2'-Chloro-4-biphenylyl)-ethylthio]-acetic acid methyl ester 294 gm (1.17 mol) of 1-(2'-chloro-4-biphenylyl)-1-chloro-ethane and 149.2 gm (1.4 mol) of thioglycolic acid methyl ester were dissolved in 1 liter of dimethyl sulfoxide, and 194.3 gm (1.4 mol) of potassium carbonate were added to the solution in small portions, while stirring vigorously and cooling on ice water. After stirring the mixture for 4 hours, 3 liters of water were added. The reaction product was extracted with toluene, and after washing the extract with water and drying it over magnesium sulfate, the solvent was removed in vacuo. Yield: 359:0 gm (95.5% of theory). $R_f$-value: 0.6 on carrier 1 with cyclohexane/ethyl acetate=4:1.

2. [1-(2'-Chloro-4-biphenylyl)-ethylthio]-acetic acid 359 gm of the methyl ester thus obtained were boiled with 94.2 gm (1.68 mol) of potassium hydroxide in 1200 ml of ethanol for 1 hour. Subsequently, the mixture was evaporated in vacuo, the crystalline residue was taken up in water, and the aqueous mixture was extracted with ether to remove neutral components. By acidification, the free acid was obtained as a slowly crystallizing oil. Yield: 215.0 gm (62.5% of theory); m.p. 114°–119° C. (from toluene).

The following compound was prepared in analogous manner:

[1-(2-Fluoro-4-biphenylyl)-ethylthio]-acetic acid, m.p. 146°–149° C. (from toluene).

EXAMPLE F

[1-(4'-Methoxy-4-biphenylyl)-ethylthio] acetic acid methyl ester (4'-Methoxy-4-biphenylyl)-methyl-ketone [see W.S. Johnson et al, J. Amer. Chem Soc. 68, 1648 (1946)] was reduced with sodium borohydride to 1-(4'-methoxy-4-biphenylyl)ethanol (m.p. 120°–122° C., from cyclohexane), and the carbinol was converted into 1-(4'-methoxy-4-biphenylyl)-1-chloroethane, m.p. 122°–124° C. (from cyclohexane), with hydrogen chloride. 5.2 gm of 1-(4'-methoxy-4-biphenylyl)-1-chloroethane (0.021 mol) were admixed in 21 ml of dry dimethyl sulfoxide with 2.7 gm (0.026 mol) of thioglycolic acid methyl ester and then with 3.5 gm (0.026 mol) of dry potassium carbonate. The mixture was stirred at room temperature for 45 minutes. The reaction product was precipitated with water, suction-filtered off, washed and dried. Yield: 6.8 gm (100% of theory): m.p. 59°–61° C.

A sample recrystallized from cyclohexane, analized as follows: $C_{18}H_{20}O_3S$; mol.wt. 316.43: Calculated: C—68.33%; H—6.37%; S—10.13%. Found: C—68.00%; H—6.52%; S—10.27%.

The following compounds were prepared in analogous manner:

[1-(4'-Fluoro-4-biphenylyl)-ethylthio] acetic acid methyl ester, oil, $R_f$-value: 0.6 on carrier 1 with petroleum ether/ethyl acetate=3:1, yield: 99% of theory.

[1-(4'-Chloro-4-biphenylyl)-ethylthio] acetic acid methyl ester, oil, $R_f$-value: 0.5 on carrier 1 with cyclohexane/ethyl acetate=4:1, yield: 95% of theory.

[1-(4'-Chloro-4-biphenylyl)-ethylthio] acetic acid, m.p. 130° C. (from toluene); yield: 78% of theory.

[1-(4'-Bromo-4-biphenylyl)-ethylthio] acetic acid methyl ester, yield: 79% of theory; m.p. 46°–49° C. (from isopropanol).

[1-(4'-Methyl-4-biphenylyl)-ethylthio] acetic acid methyl ester, oil, $R_f$-value: 0.8 on carrier 1 with petroleum ether/ethyl acetate=7:3.

Therefrom by hydrolysis:

[1-(Methyl-4-biphenylyl)-ethylthio] acetic acid, crystalline material of $R_f$-value 0.4 on carrier 1 with petroleum ether/ethyl acetate=7:3, yield: 41% of theory.

[1-(4'-Methylmercapto-4-biphenylyl)-ethylthio] acetic acid methyl ester, yield: 83.4% of theory; m.p. 74°–76° C. (from ethanol).

[1-(3'-Chloro-4-biphenylyl)-ethylthio] acetic acid methyl ester, oil, $R_f$-value: 0.55 on carrier 1 with cyclohexane/ethyl acetate=4:1; yield: 93% of theory.

[1-(2',4'Dichloro-4-biphenylyl)-ethylthio] acetic acid methyl ester, oil, $R_f$-value: 0.4 on carrier 1 with petroleum ether/ethyl acetate=7:3; yield: 76% of theory.

[1-(2,2'-Difluoro-4-biphenylyl)-ethylthio] acetic acid methyl ester, oil, $R_f$-value: 0.5 on carrier 1 with cyclohexane/ethyl acetate=4:1; yield: 94% of theory.

EXAMPLE G

[1-(2'-Cyano-4-biphenylyl)-ethylthio] acetic acid methyl ester (a) [1-(2'-Amino-4-biphenylyl)-ethylthio] acetic acid methyl ester.

22.0 gm (0.66 mol) of [1-(2'-nitro-4-biphenylyl)-ethylthio]-acetic acid methyl ester were hydrogenated in 220 ml of ethanol in the presence of 10 gm of Raney nickel at room temperature and at a hydrogen pressure of 5 atmospheres. After the absorption of hydrogen had ceased, the catalyst was suction-filtered off, and the filtrate was evaporated. The residue was an oil, $R_f$-value: 0.3 on carrier 1 with cyclohexane/ethyl acetate=4:1; yield: 18.2 gm (91% of theory).

(b) [1-(2'-Cyano-4-biphenylyl)-ethylthio] acetic acid methyl ester 18.2 gm (0.0605 mol) of the methyl ester were admixed with 15.3 ml of hydrochloric acid and 30 ml of water in 20 ml of tetrahydrofuran, and diazotized at 0°–5° C. with 4.4 gm (0.0635 mol) of sodium nitrite in 10 ml of water. The diazonium salt solution was added to a warm solution of 60° C. of $K_2[Cu(CN)_3]$ (prepared from 18 gm of CuSO₄. 5H₂, 5.1 gm NaHSO₃ and 5.1 gm KCN, and dissolving of the CuCN-precipitate in a solution of 9.4 gm of KCN in 25 ml of water). The reaction product precipitated as a brown oil, accompanied by nitrogen evolution. The product was refluxed for a short time, cooled and extracted with ethyl acetate. The evaporation residue of the extract (15.2 gm) was purified by chromatography on 900 gm of silicagel with cyclohexane/ethyl acetate=4:1. The fractions with an R$_f$-value of 0.45 on carrier 2 with cyclohexane/ethyl acetate=4:1 were combined and evaporated. Yield: 7.0 gm of an oil (37% of theory) IR-spectrum (in methylene chloride): Cn at 2210 cm$^{-1}$, ester-CO at 1730 cm$^{-1}$, UV-spectrum (in ethanol): maxima at 260 and 290 nm (log ε=4.1 and 3.8, respectively).

Preparation of end products of the formula I:

EXAMPLE 1

Diastereoisomeric
[1-(2'-fluoro-4-biphenylyl)-ethylsulfinyl]-acetic acids (a) Difficulty soluble isomer A suspension of 1477 gm (5.1 mol) of [1-(2'-fluoro-4-biphenylyl)-ethylthio]-acetic acid in 5.1 liter of glacial acetic acid was admixed over a period of 30 minutes at 15° C. with 495 gm (5.35 mol) of 36.8% hydrogen peroxide, while vigorously stirring. Subsequently, the temperature of the mixture was allowed to rise to 20° C. The starting material dissolved almost completely during the reaction, and after some time the reaction product crystallized out. After standing overnight, the product was suction-filtered off, washed with glacial acetic acid and then with petroleum ether, and dried at 40° C. Yield: 994 gm (63% OF THEORY); m.p. 164°–165° C. (decomp.).

Analysis: $C_{16}H_{15}FO_3S$; mol.wt. 306.37: Calculated: C—62.73%; H—4.94%; S—10.47%. Found: C—62.90%; H—5.03%; S—10.70%.

NMR-spectrum (deutero-dimethyl sulfoxide):
CH₃: Doublet at 1.7 ppm
CH: Quartet at 4.38 ppm (J$_{H,CH^3}$=7Hz)
CH₂: Double doublet at 3.65 ppm; (δτ=about 18 Hz; J=14 Hz)

(b) Easily soluble isomer

The acetic acid filtrate obtained in the separation of the difficulty soluble isomer was admixed with 5.1 liters of water. The obtained crystals were suction-filtered off and dried. 80 gm of the obtained 446 gm of the product were recrystallized three times from ethyl acetate. Yield: 29 gm; m.p. 149°–150° C. (decomp.).

Analysis: $C_{16}H_{15}FO_3S$; mol. wt. 306.37: Calculated: C—62.73%; H—4.94%; S—10.47%. Found: C—63.00%; H—5.06%; S—10.60%.

NMR-spectrum (deutero-dimethyl sulfoxide):
CH₃: Doublet at 1.7 ppm
CH: Quartet at 4.25 ppm (J$_{H,CH^3}$=7Hz)
CH₂: Double doublet at 3.48 ppm; (δτ=about 36 Hz; J=15 Hz).

EXAMPLE 2

[1-(2'-Fluoro-4-biphenylyl)-ethylsulfinyl]-acetic acid, difficulty soluble isomer Separation into the optically active antipodes A solution of 53.5 gm (0.175 mol) of [1-(2'-fluoro-4-biphenylyl)-ethylsulfinyl]-acetic acid, m.p. 164°–165° C. (decomp.), in 400 ml of chloroform/ethanol=3;1, was admixed with a solution of 51.5 gm (0.175 mol) of cinchonidine ([α]$_D^{20}$= −178°) in 400 ml of chloroform/ethanol=3:1. The clear solution of the salt was evaporated, and the foamy residue was dissolved in 500 ml of hot benzene. Upon standing overnight, the levorotatory acid crystallized out as its cinchonidine salt. This salt was suction-filtered off (72.0 gm, m.p. 140°–144° C.) and recrystallized from 4 liters of cyclohexane/ethanol=8:1. 40.5 gm (77% of theory) of the cinchonidine salt, m.p. 146°–148° C. (decomp.) were obtained. By acidification and recrystallization from isopropanol, the free levorotatory acid, m.p. 168°–170° C., [α]$_D^{20}$= −131.5° (c=0.5, methanol), was obtained.

From the benzene filtrate of the cinchonidine-salt-precipitation gm of the free dextrorotatory acid, m.p. 165°–167° C., [α]$_D^{20}$= +100° (c=0.5, methanol), were obtained by acidification and recrystallization from isopropanol.

EXAMPLE 3

[1-(2'-Fluoro-4-biphenylyl)-propylsulfinyl]-acetic acid, was prepared analogous to Example 1 from [1-(2'-fluoro-4-biphenylyl)-propylthio]-acetic acid by oxidation with hydrogen peroxide in glacial acetic acid. Yield: 55.4% of theory; m.p. 136°–137° (ethyl acetate).

Analysis: $C_{17}H_{17}FO_3S$; mol.wt. 320.39: Calculated: C—63.73%; H—5.35%; S—10.01%. Found: C—63.90%; H—5.52%; S—10.05%.

EXAMPLE 4

[2-(2'-Fluoro-4-biphenylyl)-propylsulfinyl]-acetic acid, was prepared analogous to Example 1 from [2-(2'-fluoro-4-biphenylyl)-propylthio]-acetic acid by oxidation with hydrogen peroxide in glacial acetic acid. Yield: 20.2% of theory; m.p. 156°–158° C. (decomp.; from n-propanol).

Analysis: $C_{17}H_{17}FO_3S$; mol.wt. 320.38: Calculated: C—63.73%; H—5.35%; S—10.01%. Found: C—63.90%; H—5.44%; S—9.96%.

NMR-spectrum (in deutero dimethyl sulfoxide and deuterochloroform):
CH₃: Doublet at 1.45 ppm (J=6 Hz),
CH+CH₂ at 3.25 ppm,
CH₂: Double doublet at 3.78 ppm (J=15 Hz).

EXAMPLE 5

[1-(2'-Fluoro-4-biphenylyl)-ethylsulfinyl]-acetic acid methyl ester 800 gm (2.61 mol) of the difficultly soluble diastereoisomer of [1-(2'-fluoro-4-biphenylyl)-ethylsulfinyl]-acetic acid, m.p. 164°–165° C., were suspended in 4 liters of benzene and 125.5 gm (3.92 mol) of methanol, and a solution of 648 gm (3.14 mol) of dicyclohexyl-carbodiimide in 650 ml of benzene was added while stirring and cooling at 20°–25° C. The acid dissolved, and dicyclohexylurea precipitated out. The mixture was allowed to stand overnight at room temperature, then the excess of carbodiimide was decomposed by addition of glacial acetic acid, and then 2 liters of water were added, the dicyclohexylurea was suction-filtered off, the organic phase was separated from the filtrate and evaporated in vacuo after drying. The obtained oil (969 gm) was recrystallized from 2.9 liters of isopropanol. Yield: 736 gm (88% of theory); m.p. 75°–77° C.

After a further recrystallization from benzene/cyclohexane=⅓ the compound had a m.p. of 78°–80° C.

Analysis: $C_{17}H_{17}FO_3S$; mol.wt 320.36: Calculated: C—63.73%; H—5.34%; S—10.01%. Found: C—63.90%; H—5.43%; S—10.21%.

NMR-spectrum (in deuterochloroform):
CH$_3$: Doublet at 1.75 ppm (J=7.2 Hz)
CH: Quartet at 4.22 ppm (J$_H$, CH$_3$=7.2 Hz)
CH$_2$: Double doublet at 3.48 ppm δτ=about 16 Hz (J=14 Hz)

EXAMPLE 6

[1-(2'-Fluoro-4-biphenylyl)-ethylsulfinyl]-acetic acid methyl ester, was prepared analogous to Example 5 from [1-(2'-fluoro-4-biphenylyl)-ethylsulfinyl]-acetic acid, m.p. 149°–150° C., with methanol and dicyclohexylcarbodiimide in benzene. Yield: 67.4% of theory; m.p. 92°–94° C. (cyclohexane/benzene=3/1).

Analysis: C$_{17}$H$_{17}$FO$_3$S; mol.wt. 320.36: Calculated: C—63.70%; H—5.34%; S—10.01%. Found: C—63.90%; H—5.39%; S—10.28%.

NMR-spectrum (in deuterochloroform):
CH$_3$: Doublet at 1.8 ppm (J=7.2 Hz)
CH: Quartet at 4.1 ppm (J$_H$, CH$_3$=7.2 Hz)
CH$_2$: Singlet at 3.31 ppm

EXAMPLE 7

Levorotatory [1-(2'-fluoro-4-biphenylyl)-ethylsulfinyl]-acetic acid methyl ester, was prepared analogous to Example 5 from levorotatory [1-(2'-fluoro-4-biphenylyl)-ethylsulfinyl]-acetic acid ([α]$_D^{20}$=−131.5°) with methanol and dicyclohexylcarbodiimide in benzene, followed by purification by column chromatography on silicagel with benzene/ethyl acetate=1/1. Yield: 87.5% of theory; m.p. 52°–54° C. (cyclohexane/benzene=3'1); [α]$_D^{20}$=−179.5° (c=0.5, methanol).

EXAMPLE 8

Dextrorotatory [1-(2'fluoro-4-biphenylyl)-ethylsulfinyl]-acetic acid methyl ester, was prepared analogous to Example 5 from dextrorotatory [1-(2'-fluoro-4-biphenylyl)-ethylsulfinyl]-acetic acid ([α]$_D^{20}$=+100°) with methanol and dicyclohexylcarbodiimide in benzene, followed by purification by column chromatography on silicagel with benzene/ethyl acetate=1/1. Yield: 87.5% of theory; oil, [α]$_D^{20}$=+112.0° (c=0.5, methanol), R$_f$-value; 0.3 (silicagel-polygram-plates with benzene/ethyl acetate=1/1), m.p. 50°–52° C. (from cyclohexane/benzene=4/1).

EXAMPLE 9

[1-(2'-Fluoro-4-biphenylyl)-ethylsulfinyl]-acetic acid isopropyl ester, was prepared analogous to Example 5 from [1-(2'-fluoro-4-biphenylyl)-ethylsulfinyl]-acetic acid, m.p. 164°–165° C., with isopropanol and dicyclohexylcarbodiimide in benzene. Yield: 91% of theory, m.p. 114°–119° C. (cyclohexane).

Analysis: C$_{19}$H$_{21}$FO$_3$S; mol.wt. 348.44: Calculated: C—65.50%; H—6.08%; S—9.20%. Found: C—65.70%; H—6.39%; S—9.00%.

NMR-spectrum (in deuterochloroform):
CH$_3$: Doublet at 1.75 ppm (J=7 Hz)
CH: Quartet at 4.2 ppm (J$_H$, CH$_3$=7 Hz)
CH$_2$: Double doublet at 3.45 ppm (J=14 Hz).

EXAMPLE 10

[1-(2'-Fluoro-4-biphenylyl)-ethylsulfinyl]-acetic acid n-butyl ester, was prepared analogous to Example 5 from [1-(2'-fluoro-4-biphenylyl)-ethylsulfinyl]-acetic acid, m.p. 164°–165° C., with n-butanol and dicyclohexylcarbodiimide in benzene, followed by purification by column chromatography on silicagel with cyclohexane/ethyl acetate=1/1. Yield: 80% of theory; m.p. 74°–75° C. (cyclohexane).

Analysis: C$_{20}$H$_{23}$FO$_3$S; mol.wt. 362.46: Calculated: C—66.28%; H—6.40%; S—8.84%. Found: C—66.50%; H—6.51%; S—8.82%.

NMR-spectrum (in deuterochloroform)
CH$_3$: Doublet at 1.77 ppm (J=7 Hz)
CH: Quartet at 4.2 ppm (J=7 Hz)
CH$_2$: Double doublet at 3.48 ppm (J=14 Hz)

EXAMPLE 11

[1-(2'-Fluoro-4-biphenylyl)-ethylsulfinyl]-acetic acid isobutyl ester, was prepared analogous to Example 5 from [1-(2'-fluoro-4-biphenylyl)-ethylsulfinyl)-acetic acid, m.p. 164°–165° C., with isobutanol and dicyclohexylcarbodiimide in benzene, followed by purification by column chromatography on silicagel with cyclohexane/ethyl acetate=1/1. Yield: 77% of theory; m.p. 81°–83° C. (cyclohexane).

Analysis: C$_{20}$H$_{23}$FO$_3$S; mol. wt. 362.46: Calculated: C—66.28%; H—6.40%; S—8.84%. Found: C—66.20%; H—6.47%; S—8.54%.

NMR-spectrum (in deuterochloroform)
CH$_3$: Doublet at 1.75 ppm (J=7 Hz)
CH: Quartet at 4.22 ppm (J=7 Hz)
CH$_2$: Double doublet at 3.48 ppm (J=14 Hz)

EXAMPLE 12

[1-(2'-Fluoro-4-biphenylyl)-ethylsulfinyl]-acetic acid isoamyl ester, was prepared analogous to Example 5 from [1-(2'-fluoro-4-biphenylyl)-ethylsulfinyl]-acetic acid, m.p. 164°–165° C., with isoamyl alcohol and dicyclohexylcarbodiimide in benzene. Yield: 80.5% of theory; m.p. 74°–76° C. (petroleum ether).

Analysis: C$_{21}$H$_{25}$FO$_3$S; mol.wt. 376.49: Calculated: C—67.00%; H—6.69%; S—8.52%. Found: C—67.30%; H—6.86%; S—8.71%.

EXAMPLE 13

[1-(2'-Fluoro-4-biphenylyl)-ethylsulfinyl]-acetic acid n-hexyl ester, was prepared analogous to Example 5 from [1-(2'-fluoro-4-biphenylyl)-ethylsulfinyl]-acetic acid, m.p. 164°–165° C., with n-hexanol and dicyclohexylcarbodiimide in benzene, followed by purification by column chromatography on silicagel with cyclohexane/ethyl acetate=1/1. Yield: 58% of theory; oil, R$_f$-value: 0.5 (cyclohexane/ethyl acetate=1/1 on preprepared silicagel plates); m.p. 51°–53° C. (from petroleum ether).

Analysis: C$_{22}$H$_{27}$FO$_3$S; mol.wt. 390.52: Calculated: C—67.66%; H—6.97%; S—8.21%. Found: C—67.70%; H—7.17%; S—8.32%.

EXAMPLE 14

[1-(2'-Fluoro-4-biphenylyl)-ethylsulfinyl]-acetic acid benzyl ester, was prepared anlogous to Example 5 from [1-(2'fluoro-4-biphenylyl)-ethylsulfinyl]-acetic acid, m.p. 164°–165° C., with benzyl alcohol and dicyclohexylcarbodiimide in benzene. Yield: 85% of theory; m.p. 123°–125° C. (cyclohexane-benzene).

Analysis: C$_{23}$H$_{21}$FO$_3$S; mo.wt. 396.48: Calculated: C—69.67%; H—5.34%; S—8.09%. Found: C—69.90%; H—5.75%; S—8.05%.

EXAMPLE 15

[2-(2'-Fluoro-4-biphenylyl)-propylsulfinyl]-acetic acid methyl ester, was prepared analogous to Example 5 from [2-(2'-fluoro-4-biphenylyl)-propylsulfinyl]-acetic acid, m.p. 156°–158° C., with methanol and dicyclohexylcarbodiimide in benzene, followed by purification by column chromatography on silicagel with toluene/ethyl acetate=½. Yield: 31.7% of theory; m.p. 127°–129° C. (n-butanol).

Analysis: $C_{18}H_{19}FO_3S$; mol.wt. 334.42: Calculated: C—64.65%; H—5.73%; S—9.59%. Found: C—64.90%; H—5.84%; S—9.71%.

EXAMPLE 16

[1-(2′-Fluoro-4-biphenylyl)-ethylsulfinyl]-acetic acid methyl ester 10 gm (0.033 mol) of [1-(2′-fluoro-4-biphenylyl)-ethylsulfinyl]-acetic acid, m.p. 164°–165° C., were suspended in 100 ml of methanol, and 3 ml of phosphorus oxychloride were added dropwise while cooling at 10° C. The mixture was allowed to stand at room temperature for 2 hours, and then the reaction was caused to go to completion by heating to 35° C. The reaction product was precipitated with water and extracted with benzene. The organic extract was evaporated, and the residue was purified by chromatography on silicagel (grain size: 0.05–0.2 mm) with benzene/cyclohexane=1/1. The fractions with an $R_f$-value of 0.4 were combined and evaporated, and the residue (6.0 gm) was recrystalized from cyclohexane/benzene=3/1. Yield: 4.4 gm (41.5% of theory); m.p. 78°–79° C.

When a corresponding amount of thionyl chloride was used instead of phosphorus oxychloride, the ester was obtained with a yield of 63% of theory.

EXAMPLE 17

[1-(2′-Fluoro-4-biphenylyl)-ethylsulfinyl]-acetic acid ethyl ester, was prepared analogous to Example 16 from [1-(2′-fluoro-4-biphenylyl)-ethylsulfinyl]-acetic acid, m.p. 164°–165° C., with ethanol in the presence of phosphorus oxychloride, followed by purification by column chromatography on silicagel with benzene/cyclohexane=1/1. Yield: 28.2% of theory; m.p. 84°–85° C. (cyclohexane).

Analysis: $C_{18}H_{19}FO_3S$; mol.wt. 334.42: Calculated: C—64.65%; H—5.73%; S—9.59%. Found: C—64.60%; H—5.80%; S—9.38%.

EXAMPLE 18

[1-(2′-Fluoro-4-biphenylyl)-ethylsulfinyl]-acetic acid n-propyl ester, was prepared analogous to Example 16 from [1-(2′-fluoro-4-biphenylyl)-ethylsulfinyl]-acetic acid, m.p. 164°–165° C., with n-propanol in the presence of thionyl chloride, followed by purification by column chromatography on silicagel with benzene/cyclohexane=1/1. Yield: 15.5% of theory; m.p. 55°–57° C. (cyclohexane/benzene=5/1).

Analysis: $C_{19}H_{21}FO_3S$; mol. wt. 348.44: Calculated: C—65.50%; H—6.08%. Found: C—65.30%; H—6.30%.

EXAMPLE 19

[1-(2′-Fluoro-4-biphenylyl)-ethylsulfinyl]-acetic acid methyl ester 3 gm (10 millimols) of [1-(2′-fluoro-4-biphenylyl)-ethylsulfinyl]-acetic acid, m.p. 164°–165° C., were dissolved in 15 ml of dimethyl sulfoxide, 2 gm of potassium carbonate and 1.5 ml of methyl iodide were added, and the mixture was stirred at room temperature for one hour. Subsequently, the mixture was diluted with water, hydrochloric acid was added and the reaction product was extracted with ethyl acetate. After washing, drying and evaporating the extract, the residue was recrystalized from isopropanol (10 ml). Yield: 1.4 gm (44% of theory); m.p. 79° C.

EXAMPLE 20

[1-(4-Biphenylyl)-ethylsulfinyl]-acetic acid methyl ester, was prepared analogous to Example 1 from [1-(4-biphenylyl)-ethylthio]-acetic acid methyl ester and hydrogen peroxide in glacial acetic acid. Yield: 31% of theory; m.p. 86°–87° C. (benzene/cyclohexane=⅓).

Analysis: $C_{17}H_{18}O_3S$; mol.wt. 302.40: Calculated: C—67.52%; H—6.00%; S—10.60%. Found: C—67.60%; H—5.97%; S—10.63%.

NMR-spectrum (in deuterochloroform):
$CH_3$: Doublet at 1.75 ppm (J=7 Hz)
CH: Quartet at 4.2 ppm (J=7 Hz)
$CH_2$: Double doublet at 3.45 ppm (J=14 Hz)

EXAMPLE 21

[1-(2′-Fluoro-4-biphenylyl)-ethylsulfinyl]-acetic acid methyl ester, was prepared analogous to Example 1 from [1-(2′-fluoro-4-biphenylyl)-ethylthio]-acetic acid methyl ester by oxidation with hydrogen peroxide in glacial acetic acid. The separation of the two diastereoisomeric esters was carried out by column chromatography on silicagel (grain size: 0.05–0.2 mm) with a ratio of substance/silicagel=1/60; eluant; cyclohexane/ethyl acetate=⅓). Yield: 12% of theory of one diastereoisomer of [1-(2′-fluoro-4-biphenylyl)-ethylsulfinyl]-acetic acid methyl ester, m.p. 92°–94° C., and 14% of theory of the other diastereoisomer of [1-(2′-fluoro 4-biphenylyl)-ethylsulfinyl]-acetic acid methyl ester, m.p. 77°–78° C.

EXAMPLE 22

[1-(2′-Fluoro-4-biphenylyl)-propylsulfinyl]-acetic acid methyl ester, was prepared analogous to Example 1 from [1-(2′-fluoro-4-biphenylyl)-propylthio]-acetic acid methyl ester by oxidation with hydrogen peroxide in glacial acetic acid, followed by purification by column chromatography on silicagel with benzene/ethyl acetate=1/1. Yield: 94.6% of theory; oil, $R_f$-value: 0.4+0.5 with benzene/ethyl acetate=1/1 silicagel-polygram (double spot).

Analysis: $C_{18}H_{19}FO_3S$; mol.wt. 334.42: Calculated: C—64.65%; H—5.73%; S—9.59%. Found: C—65.00%; H—5.88%; S—9.35%.

EXAMPLE 23

[3-(4-Biphenylyl)-butylsulfinyl]-acetic acid methyl ester, was prepared analogous to Example 1 from [3-(4-biphenylyl)-butylthio]-acetic acid methyl ester by oxidation with hydrogen peroxide in glacial acetic acid. Yield: 97% of theory; oil, $R_f$-value: 0.32 (ethyl acetate on silicagel-polygram-plates).

Analysis: $C_{19}H_{22}O_3S$ mol.wt. 330.45: Calculated: C—69.06%; H—6.71%; S—9.70%. Found: C—69:00%; H—6.92%; S—9.40%.

EXAMPLE 24

[3-(2′-Fluoro-4-biphenylyl)-butylsulfinyl]-acetic acid methyl ester, was prepared analogous to Example 1 from [3-(2′-fluoro-4-biphenylyl)-butylthio]-acetic acid methyl ester by oxidation with hydrogen peroxide in glacial acetic acid. Yield: 93% of theory; oil, $R_f$-value: 0.42 (benzene/ethyl acetate=2/1).

Analysis: $C_{19}H_{21}FO_3S$; mol.wt. 348.44: Calculated: C—65.50%; H—6.07%; S—9.20%. Found: C—65.20%; H—6.17%; S—9.07%.

EXAMPLE 25

[1-(2′-Fluoro-4-biphenylyl)-ethylsulfinyl]-acetic acid methyl ester 306 mgm (1 millimol) of [1-(2′-fluoro-4-biphenylyl)-ethylsulfinyl]-acetic acid and 0.15 ml of triethylamine were dissolved in 2 ml of chloroform, and 0.15 ml of chloroformic acid methyl ester was added to the solution at room temperature. After 30 minutes of standing, the mixture was washed with water, dried and evaporated, and the residue was recrystallized from 1 ml of isopropanol. Yield: 200 mgm (62.5% of theory); m.p. 75°–78° C.

EXAMPLE 26

[1-(2′-Fluoro-4-biphenylyl)-ethylsulfinyl]-acetic acid methyl ester 1.5 gm (50 millimols) of [1-(2′-fluoro-4-biphenylyl)-ethylsulfinyl]-acetic acid, m.p. 164°–165° C., were dissovled in 3 ml of methanol and 1.2 ml of 2,2-dimethoxypropane, 100 mgm of p-toluenesulfonic acid were added to the solution, and the mixture was allowed to stand for 12 days at room temperature. Then, water was added and the ester was extracted with toluene. The organic extract was washed with water, dried and evaporated, and the residue was purified by chromatography on 75 gm of silicagel (grain size 0.05–0.2 mm) with cyclohexane/ethyl acetate—¼. The combined ester—containing fractions were evaporated, and the residue was recrystallized from 3 ml of isopropanol. Yield: 800 mgm (50% of theory); m.p. 77°–79° C.

EXAMPLE 27

[1-(2′-Fluoro-4-biphenylyl)-ethylsulfinyl]-acetic acid-n-butyl ester 1.5 gm (5 millimols) of [1-(2′-fluoro-4-biphenylyl)-ethylsulfinyl]-acetic acid, m.p. 164°–165° C., were stirred with 1.05 gm of potassium carbonate and 0.9 ml of n-butyl bromide in 15 ml of dimethyl sulfoxide for 60 hours. The mixture was subsequently diluted with water, and the reaction product was extracted with toluene. After washing, drying and evaporating the extract, the residue (1.7 gm) was recrystallized from cyclohexane. Yield: 1.2 gm (67% of theory); m.p.: 72°–74° C.

EXAMPLE 28

[1-(2′-Fluoro-4-biphenylyl)-ethylsulfinyl]-acetic acid-n-butyl ester, was prepared analogous to Example 27 from [1-(2′-fluoro-4-biphenylyl)-ethylsulfinyl]-acetic acid, m.p. 164°–165° C., and tri-n-butyl-phosphate in the presence of calcium oxide in dimethyl sulfoxide. Yield: 58% of theory; m.p.: 71°–73° C.

EXAMPLE 29

[1-(2′-Fluoro-4-biphenylyl)-ethylsulfinyl]-acetic acid methyl ester

A solution of 320 mgm (7.6 millimols) of diazomethane (prepared from 2.14 gm of p-toluenesulfonyl-methylnitrosoamide in 30 ml of ether and 0.4 gm of potassium hydroxide in 10 ml of 96% ethanol and subsequent distillation) was added, while stirring, to a suspension of 2.3 gm (7.5 millimols) of [1-(2′-fluoro-4-biphenylyl)-ethylsulfinyl]-acetic acid (m.p.: 164°–165° C.) in 20 ml of ether. The acid dissolved, accompanied by nitrogen evolution. After the reaction was finished, the mixture was evaporated, and the residue was recrystallized from benzene cyclohexane (1/5). Yield: 2.0 gm (83.5% of theory); m.p.: 75°–77° C.

EXAMPLE 30

[1-(2′-Fluoro-4-biphenylyl)-ethylsulfinyl]-acetic acid ethyl ester, was prepared analogous to Example 29 from [1-(2′-fluoro-4-biphenylyl)-ethylsulfinyl]-acetic acid, m.p. 164°–165° C., and diazoethane in ether. Yield: 78% of theory; m.p.: 82°–84° C.

EXAMPLE 31

[1-(2′-Fluoro-4-biphenylyl)-ethylsulfinyl]-acetic acid methyl ester 1.1 gm (3 millimols) of tetrabutylammonium iodide and 3.06 gm (10 millimols) of [1-(2′-fluoro-4-biphenylyl)-ethylsulfinyl]-acetic acid (m.p. 164°–165° C.) were added to a solution of 730 mgm (13 millimols) of potassium hydroxide in 20 ml of water, then 20 ml of chloroform and 2 ml of methyl iodide were added, and the mixture was stirred at room temperature for 10 hours. Afterwards, the organic phase was separated from the neutral aqueous phase, washed with dilute hydrochloric acid and then with water, dried and evaporated. The residue (3.6 gm) was purified by chromatography on 100 gm of silicagel (grain size: 0.05–0.2 mm) with cyclohexane ethyl acetate=¼. After evaporation of the combined fractions with an $R_f$-value of 0.4 and recrystallization of the residue from isopropanol, 1.7 gm (53% of theory) of the title compound m.p. 75°–77° C. were obtained.

EXAMPLE 32

[1-(2′-Fluoro-4-biphenylyl)-ethylsulfinyl]-acetic acid methyl ester, was prepared analogous to Example 27 from [1-(2′-fluoro-4-biphenylyl)-ethylsulfinyl]-acetic acid, m.p. 164°–165° C., and dimethyl sulfate in the presence of potassium carbonate in acetone. Yield: 68% of theory; m.p.: 75°–77° C.

EXAMPLE 33

[1-(2′-Chloro-4-biphenylyl)-ethylsulfinyl]-acetic acid 50 gm (0.163 mol) of [1-(2′-chloro-4-biphenylyl)-ethylthio]-acetic acid were suspended in 163 ml of glacial acetic acid and 16.0 gm (0.171 mol) of 36.3% hydrogen peroxide were added dropwise to the suspension at 10° C. while vigorously stirring. Afterwards, the mixture was allowed to stand overnight at room temperature, during which time the starting compound dissolved. Subsequently, 500 ml of water were added, the reaction product was extracted with ethyl acetate, and the organic solvent was removed from the extract in vacuo, leaving 45.1 gm (85% of theory) of the title compound, m.p. 144°–147° C. (from ethyl acetate).

Analysis: $C_{16}H_{15}ClO_3S$; mol. wt. 322.82: Calculated: C—59.53%; H—4.68%; Cl—10.98%; S—9.93%. Found: C—59.50%; H—4.89%; Cl—10.98%; S—9.76%.

$CH_3$: Doublet at 1.8 ppm
CH: Quartet at 4.25 ppm ($J_H$, $CH_3$=7 Hz)
$CH_2$: Doublet at 3.5 ppm

EXAMPLE 34

[1-(2'-Chloro-4-biphenylyl)-ethylsulfinyl]-acetic acid methyl ester

A solution of 19.9 gm (0.059 mol) of [1-(2'-chloro-4-biphenylyl)-ethylsulfinyl]-acetic acid and 12.5 gm (0.088 mol) of methyl iodide in 120 ml of dry dimethyl sulfoxide was admixed with 12.2 gm (0.088 mol) of dry potassium carbonate, and the mixture was stirred at room temperature for 19 hours. The crude reaction product was precipitated with water and extracted with ethyl acetate (yield: 23.1 gm). For purification, the obtained crude product was purified by chromatography on 1200 gm of silicagel with cyclohexane ethyl acetate=1/1. The combined fractions with an $R_f$-value of 0.23 (on carrier 2) were combined and evaporated, leaving 6.2 gm (31.2% of theory) of the title compound; oil, $R_f$-value: 0.23 on carrier 1 with cyclohexane/ethyl acetate=1/1.

Analysis: $C_{17}H_{17}ClO_3S$; mol. wt. 336.85: Calculated: C—60.62%; H—5.09%; Cl—10.53%; S—9.52%. Found: C—60.90%; H—5.66%; Cl—9.68%; S—8.54%.

EXAMPLE 35

[1-(2'-Chloro-4-biphenylyl)-ethylsulfinyl]-acetic acid ethyl ester, was prepared analogous to Example 34 from [1-(2'-chloro-4-biphenylyl)-ethylsulfinyl]-acetic acid and ethyl iodide in dimethyl sulfoxide in the presence of potassium carbonate. The diastereoisomers were separated by column chromatography on silicagel with cyclohexane/ethyl acetate=1/1.

1st Diastereoisomer:

Oil. $R_f$-value: 0.4 on carrier 2 with cyclohexane/ethyl acetate=1/1; yield: 11% of theory.

Analysis: $C_{18}H_{19}ClO_3S$; mol. wt. 350.86: Calculated: C—61.62%; H—5.46%; Cl—10.12%; S—9.14%. Found: C—61.90%; H—5.79%; Cl—9.14%; S—8.31%.

NMR-spectrum (in $CDCl_3$):

$CH_2$: Singlet at 3.3 ppm

2nd Diastereoisomer:

Crystal, m.p. 81°–82° C. (from cyclohexane).

Yield: 62.8% of theory.

$R_f$-value: 0.3 on carrier 2 with cyclohexane/ethyl acetate=1/1.

Analysis: $C_{18}H_{19}ClO_3S$; mol. wt. 350.86: Calculates: C—61.62%; H—5.46%; Cl—10.12%; S—9.14%. Found: C—61.50%; H—5.45%; Cl—10.05%; S—8.94%.

NMR-spectrum (in $CDCl_3$):

$CH_3$: Doublet at 1.8 ppm (J=7 Hz)

CH: Quartet at 4.25 ppm (J=7 Hz)

$CH_2$: Double doublet at 3.5 ppm (J=14 Hz)

EXAMPLE 36

[1-(2-Fluoro-4-biphenylyl)-ethylsulfinyl]-acetic acid, was prepared analogous to Example 33 from [1-(2-fluoro-4-biphenylyl)-ethylthio]-acetic acid by oxidation with hydrogen peroxide in glacial acetic acid. The diastereoisomers were separated on the basis of their different solubility in glacial acetic acid.

Difficulty soluble isomer:

Yield: 59% of theory; m.p. 161°–163° C. (decomp.); from glacial acetic acid.

Analysis: $C_{16}H_{15}FO_3S$; mol. wt. 306.37: Calculated: C—62.73%; H—4.94%; S—10.47%. Found: C—63.00%; H—5.07%; S—10.71%.

NMR-spectrum (in $CDCl_3$-$CD_3OD$):

$CH_3$: Doublet at 1.8 ppm (J=7 Hz)

CH: Quartet at 4.3 ppm (J=7 Hz)

$CH_2$: slightly split doublet at 3.55 ppm

Easily soluble isomer:

Yield: 16% of theory; m.p. 151°–153° C. (decomp.); from ethyl acetate.

Analysis: $C_{16}H_{15}FO_3S$; mol. wt. 306.37: Calculated: C—62.73%; H—4.94%; S—10.47%. Found: C—62.40%; H—4.94%; S—10.35%.

NMR-spectrum (in $CDCl_3$-$CD_3OD$):

$CH_3$: Doublet at 1.8 ppm (J=7 Hz)

CH: Quartet at 4.15 ppm (J=7 Hz)

$CH_2$: Doublet at 3.5 ppm (J=8 Hz)

EXAMPLE 37

[1-(2-Fluoro-4-biphenylyl)-ethylsulfinyl]-acetic acid methyl ester

A solution of 1.53 gm (5 millimols) of [1-(2-fluoro-4-biphenylyl)-ethylsulfinyl]-acetic acid, m.p. 161°–163° C., in 15 ml of benzene was admixed with 0.24 gm (7.5 millimols) of methanol, and then a solution of 1.25 gm (6 millimols) of dicyclohexyl-carbodiimide in 5 ml of benzene was added. After stirring for one hour, the precipitated dicyclohexylurea was suction-filtered off, the filtrate was evaporated, and the residue was purified by chromatography on 300 gm of silicagel with cyclohexane/ethyl acetate=¼. Yield: 1.4 gm (87.6% of theory); oil, $R_f$-value: 0.5 on carrier 1 with cyclohexane/ethyl acetate=¼.

Analysis: $C_{17}H_{17}FO_3S$; mol. wt. 320.36: Calculated: C—63.73%; H—5.34%; S—10.01%. Found: C—63.70%; H—5.58%; S—10.25%.

NMR-spectrum ($CDCl_3$): $CH_2$: Doublet at 3.5 ppm.

EXAMPLE 38

[1-(2-Fluoro-4-biphenylyl)-ethylsulfinyl]-acetic acid methyl ester, was prepared analogous to Example 37 from [1-(2-fluoro-4-biphenylyl)-ethylsulfinyl]-acetic acid, m.p. 151°–153° C.; yield: 44% of theory; m.p. 88°–92° C. (from cyclohexane/benzene=4/1).

Analysis: $C_{17}H_{17}FO_3S$; mol. wt. 320.36: Calculated: C—63.73%; H—5.34% S—10.01%. Found: C—63.80%; H—5.72%; S—9.84%.

EXAMPLE 39

[1-(2'-Fluoro-4-biphenylyl)-ethylsulfinyl]-acetic acid crotyl ester, was prepared analogous to Example 34 from [1-(2'-fluoro-4-biphenylyl)-ethylsulfinyl]-acetic acid, m.p. 164°–165° C., and crotyl chloride in dimethylsulfoxide in the presence of potassium carbonate. Yield: 83.5% of theory; oil, $R_f$-value: 0.3 on carrier 2 with cyclohexane/ethyl acetate=3/2.

Analysis: $C_{20}H_{21}FO_3S$; mol. wt. 360.44: Calculated: C—66.65%; H—5.87%; S—8.89%. Found: C—66.80%; H—6.00%; S—9.11%.

NMR-spectrum (in $CDCl_3$): $CH_2$: Double doublet at 1.5 ppm (J=13 Hz).

EXAMPLE 40

[1-(2'-Fluoro-4-biphenylyl)-ethylsulfinyl]-acetic acid (2-methoxy-ethyl)-ester

A suspension of 5.0 gm (16.4 millimols) of [1-(2'-fluoro-4-biphenylyl)-ethylsulfinyl]-acetic acid, m.p. 164°–165° C., in 50 ml of dry tetrahydrofuran was admixed with 2.92 gm (18.1 millimols) of carbonyl-diimidazole, whereupon the acid dissolved and carbon dioxide was given off. After one hour, 1.37 gm (18.1 millimols) of glycol monomethyl ether were added, and the mixture was allowed to stand for 2 hours. For isolation of the reaction product, the mixture was evaporated, and the residue was distributed between dilute hydrochloric acid and ethyl acetate, and the organic solution was purified by chromatography on 180 gm of silicagel with cyclohexane/ethyl acetate=¼. For further purification, the product mixture was recrystalized from cyclohexane/ethyl acetate=4/1. Yield: 3.8 gm (63.8% of theory); m.p. 65°–67° C.

Analysis: $C_{19}H_{21}FO_4S$; mol. wt. 364.43: Calculated: C—62.62%; H—5.81%; S—8.80%. Found: C—62.50%; H—5.85%; S—9.01%.

EXAMPLE 41

[1-(2'-Fluoro-4-biphenylyl)-ethylsulfinyl]-acetic acid allyl ester, was prepared analogous to Example 40 from [1-(2'-fluoro-4-biphenylyl)-ethylsulfinyl]-acetic acid, m.p. 164°–165° C., and allyl alcohol, followed by purification by column chromatography with cyclohexane/ethyl acetate=1/1. Yield: 67.3% of theory; m.p. 59°–61° C. (cyclohexane/ethylacetate=9/1).

Analysis: $C_{19}H_{19}FO_3S$; mol. wt. 346.42: Calculated: C—65.88%; H—5.53%; S—9.25%. Found: C—66.00%; H—5.72%; S—9.45%.

EXAMPLE 42

[1-(2'-Fluoro-4-biphenylyl)-ethylsulfinyl]-acetic acid (2-pyridylmethyl) ester, was prepared analogous to Example 40 from [1-(2'-fluoro-4-biphenylyl)-ethylsulfinyl]-acetic acid, m.p. 164°–165° C., and pyridyl-(2)-methanol. Yield: 75.5% of theory; m.p. 92°–94° C. (cyclohexane/ethyl acetate=1/1).

Analysis: $C_{22}H_{20}FNO_3S$; mol. wt. 397.47: Calculated: C—66.48%; H—5.07%; S—8.07%. Found: C—66.80%; H—5.13%; S—8.30%.

EXAMPLE 43

[1-(2'-Fluoro-4-biphenylyl)-ethylsulfinyl]-acetic acid (3-pyridylmethyl) ester, was prepared analogous to Example 40 from [1-(2'-fluoro-4-biphenylyl)-ethylsulfinyl]-acetic acid, m.p. 164°–165° C., and pyridyl-(3)-methanol. Yield: 80.3% of theory; m.p. 94°–96° C. (cyclohexane/ethyl acetate=2/1).

Analysis: $C_{22}H_{20}FNO_3S$; mol. wt. 397.47: Calculated: C—66.48%; H—5.07%; N—3.52%; S—8.07%. Found: C—66.80%; H—5.18%; N—3.41%; S—8.17%.

EXAMPLE 44

[1-(2'-Fluoro-4-biphenylyl)-ethylsulfinyl]-acetic acid phenyl ester, was prepared analogous to Example 40 from [1-(2'-fluoro-4-biphenylyl)-ethylsulfinyl]-acetic acid, m.p. 164°–165° C., and phenol. Yield: 46% of theory; m.p. 116°–118° C. (cyclohexane/ethyl acetate=4/1).

Analysis: $C_{22}H_{19}FO_3S$; mol. wt. 382.46: Calculated: C—69.09%; H—5.01%; S—8.38%. Found: C—69.25%; H—5.21%; S—8.55%.

EXAMPLE 45

Oxidation of [1-(2'-fluoro-4-biphenylyl)-ethylthio]-acetic acid into [1-(2'-fluoro-4-biphenylyl)-ethylsulfinyl]-acetic acid 1.45 gm (5 millimols) each of [1-(2'-fluoro-4-biphenylyl)-ethylthio]-acetic acid were added to the amount of solvent indicated in the following table, and the oxidizing agent was added. After the reaction, the mixture was diluted with water and, if an alkaline solvent was used, acidified. The mixture of the diastereoisomers was suction-filtered off and dried.

The ratio of the two diastereoisomers in the product was determined after thin-layer chromatographic separation of their methyl esters by evaluation of the spot intensities under the UV-lamp.

The esterification was effected in dimethyl sulfoxide with methyl iodide in the presence of potassium carbonate. In the table A = 8 l-(2'-fluoro-4-biphenylyl)-ethylsulfinyl]-acetic acid methyl ester, m.p. 78°–80° C., and B = [1-(2'-fluoro-4-biphenylyl)-ethylsulfinyl]-acetic acid methyl ester, m.p. 92°–94° C.

| Solvent | Oxidizing agent | Reaction time | Reaction temperature | Yield of diastereo-isomeric mixture | Percent ratio A/B |
|---|---|---|---|---|---|
| 25 ml of 80% pyridine | 2.0 gm of iodobenzene di chloride | 45 minutes | 0°–10° C. | 100% | 50:50 |
| 30 ml of methanol | 1.6 gm (7.5 mmols) of sodium iodate in 10 ml of water | 2 hours | 25° C. | 90% | 70:30 |
| 0.56 gm of sodium carbonate in 30 ml of water | 0.49 gm (5.25 mmols) of 36.3% hydrogen peroxide | 2 hours | 25° C. | 100% | 70:30 |
| 0.725 gm of potassium carbonate in 30 ml of water | 0.49 gm (5.25 mmols) of 36.3% hydrogen peroxide | 2 hours | 25° C. | 100% | 70:30 |
| 0.41 gm of sodium hydroxide in 30 ml of water | 0.49 gm (5.25 mmols) of 36.3% hydrogen peroxide | 2 hours | 25° C. | 100% | 60:40 |
| 0.41 gm of sodium hydroxide in 30 ml of water | 0.49 gm (5.25 mmols) of 36.3% hydrogen peroxide | 2 hours | 50° C. | 100% | 60:40 |
| 15 ml of formic acid | 0.49 gm (5.25 mmols) of 36.3% hydrogen peroxide | 2 hours | 15° C. | 90% | 70:30 |
| 15 ml of glacial acetic acid and 1.5 ml of conc. sulfuric acid | 0.49 gm (5.25 mmols of 36.3% hydrogen peroxide | 20 minutes | 15° C. | 90% | 70:30 |

EXAMPLE 46

[1-(3'-Chloro-4-biphenylyl)-ethylsulfinyl]-acetic acid methyl ester 1.4 ml of 36.4% hydrogen peroxide were added dropwise to 5.0 gm (15.5 millimols) of [1-(3'-chloro-4-biphenylyl)-ethylthio]-acetic acid methyl ester in 20 ml of glacial acetic acid. After 1 hour, the mixture was evaporated in vacuo, and the residue was diluted with water and extracted with ethyl acetate. After washing, drying and evaporating the extract, 5.2 gm of an oily residue were obtained which was passed through a 500 gm-silicagel column with cyclohexane/ethyl acetate=¼. After evaporation of the eluate, 5.0 gm (96% of theory) of the title compound were obtained as an oil with $R_f$-values of 0.4 and 0.55 (diastereoisomeric mixture) on carrier 1 with cyclohexane/ethyl acetate=¼. NMR-spectrum (CDCl$_3$): CH$_2$-signals (a) as double doublet at 3.46; (b) as singlet at 3.34 Hz.

One diastereoisomer crystallized from isopropanol; it showed the CH$_2$-group as double doublet at 3.46 ppm (J=14 Hz) in the NMR-spectrum (CDCl$_3$). Yield: 51.5% of theory; m.p. 85°-87° C.

Analysis: C$_{17}$H$_{17}$Clo$_3$S; mol. wt. 336.79: Calculated: C—60.63%; H—5.09%; Cl—10.53%; S—9.35%. Found: C—60.70%; H—5.02%; Cl—10.52%; S—9.52%.

EXAMPLE 47

[1-(4'-Fluoro-4-biphenylyl)-ethylsulfinyl]-acetic acid methyl ester, was prepared analogous to Example 46 from [1-(4'-fluoro-4-biphenylyl)-ethylthio]-acetic acid methyl ester by oxidation with hydrogen peroxide in glacial acetic acid. Yield: 70% of theory; m.p. 82°-84° C. (from isopropanol).

NMR-spectrum (CDCl$_3$): The CH$_2$-signals of the diastereoisomeric mixture appeared (a) as double doublet at 3.5 ppm, (b) as singlet at 3.33 ppm.

Analysis: C$_{17}$H$_{17}$FO$_3$S; mol. wt. 320.36: Calculated: C—63.73%; H—5.34%; S—10.01%. Found: C—64.00%; H—5.34%; S—9.70%.

EXAMPLE 48

[1-(4'-Chloro-4-biphenylyl)-ethylsulfinyl]-acetic acid, was prepared analogous to Example 46 from [1-(4'-chloro-4-biphenylyl)-ethylthio]-acetic acid by oxidation with hydrogen peroxide in glacial acetic acid. Yield: 96% of theory; m.p. of the diastereoisomeric mixture; 162°-163° C. (decomp.; from glacial acetic acid/water=15/35).

Analysis: C$_{16}$H$_{15}$ClO$_3$S; mol. wt. 322.82: Calculated: C—59.53%; H—4.68%; Cl—10.98%; S—9.93%. Found: C—59.40%; H—4.76%; Cl—11.02%; S—9.89%.

EXAMPLE 49

[1-(4'-Bromo-4-biphenylyl)-ethylsulfinyl]-acetic acid methyl ester, was prepared analogous to Example 46 from [1-(4'-bromo-4-biphenylyl)-ethylthnio]-acetic acid methyl ester by oxidation with hydrogen peroxide in glacial acetic acid.

Yield: 63% of theory; m.p. of the diastereoisomeric mixture: 119°-125° C. (from isopropanol).

NMR-spectrum (CDCl$_3$): CH$_2$-signals (a) as double doublet at 3.5 ppm; (b) as singlet at 3.33 ppm.

Analysis: C$_{17}$H$_{17}$BrO$_3$S; mol. wt. 381.31: Calculated: C—53.55%; H—4.49%; Br—20.96%; S—8.41%. Found: C—53.81%; H—4.48%; Br—21.40%; S—8.38%.

EXAMPLE 50

[1-(4'-Methoxy-4-biphenylyl)-ethylsulfinyl]-acetic acid methyl ester, was prepared analogous to Example 46 from [1-(4'-methoxy-4-biphenlyl)-ethylthio]-acetic acid methyl ester by oxidation with hydrogen peroxide in glacial acetic acid.

Yield: 53% of theory; m.p. 143°-145° C. (from ethyl acetate/cyclohexane=1/1).

NMR-spectrum (CDCl$_3$): CH$_2$-group as doublet at 3.45 ppm.

Analysis: C$_{18}$H$_{20}$O$_4$S; mol. wt. 332.43: Calculated: C—65.04%; H—6.06%; S—9.65%. Found: C—64.90%; H—6.20%; S—9.94%.

EXAMPLE 51

[1-(4'-Methyl-4-biphenylyl)-ethylsulfinyl]-acetic acid, was prepared analogous to Example 46 from [1-(4'-methyl-4-biphenylyl)-ethylthio]-acetic acid by oxidation with hydrogen peroxide in glacial acetic acid. M.p. of the isomer which is difficultly soluble in glacial acetic acid: 163°-165° C. (decomp.); yield: 43.5% of theory.

EXAMPLE 52

[1-(4'-Methyl-4-biphenylyl)-ethylsulfinyl]-acetic acid methyl ester, was prepared analogous to Example 34 from [1-(4'-methyl-4-biphenylyl)-ethylsulfinyl]-acetic acid, m.p. 163°-165° C., by esterification with potassium carbonate and methyl iodide.

Yield: 55% of theory; m.p. 103°-104° C. (from toluene/petroleum ether).

Analysis: C$_{18}$H$_{20}$O$_3$s: mol. wt. 316.41: Calculated: C—68.32%; H—6.37%; S—10.14%. Found: C—68.30%; H—6.32%; S—10.04%.

NMR-spectrum (CDCl$_3$): CH$_2$-group as double doublet at 3.44 ppm (J=15 Hz, δτ=35 Hz).

EXAMPLE 53

[1-(4'-Methylmercapto-4-biphenylyl)-ethylsulfinyl]-acetic acid methyl ester, was prepared analogous to Example 46 from [1-(4'-methylmercapto-4-biphenylyl)-ethylthio]-acetic acid methyl ester by oxidation with hydrogen peroxide in glacial acetic acid, followed by purification by column chromatography on silicagel with cyclohexane/ethyl acetate=4/1. The diastereoisomeric mixture thus obtained was an oil with an $R_f$-value from 0.3 to 0.4 on carrier 1 with cyclohexane/ethyl acetate=4/1. Yield: 67% of theory.

NMR-spectrum (CDCl$_3$): CH$_2$-signals (a) as doublet at 3.5 ppm and (b) as singlet at 3.35 ppm.

EXAMPLE 54

[1-(2,2'-Difluoro-4-biphenylyl)-ethylsulfinyl]-acetic acid methyl ester, was prepared analogous to Example 46 from [1-(2,2'-difluoro-4-biphenylyl)-ethylthio]-acetic acid methyl ester by oxidation with hydrogen peroxide in glacial acetic acid. The diastereoisomeric mixture was an oil with the $R_f$-values 0.4 and 0.5 on carrier 1 with cyclohexane/ethyl acetate=¼. Yield: 87.5% of theory.

NMRspectrum (CDCl$_3$): CH$_2$-signals as (a) double doublet at 3.55 ppm (J=15 Hz, δτ=32 Hz) and as (b) singlet at 3.35 ppm. One of the isomers with a CH$_2$-signal at 3.55 ppm (J=15 Hz) was isolated as an oil by column chromatography on 50 times its amount of silicagel with cyclohexane/ethyl acetate=¼. Yield:

10.7% of theory. $R_f$-value=0.4 on carrier 1 with cyclohexane/ethyl acetate=¼.

Analysis: $C_{17}H_{16}F_2O_3S$; mol. wt. 338.38: Calculated: C—60.34%; H—4.77%; S—9.48%. Found: C—60.50%; H—5.01%; S—9.21%.

EXAMPLE 55

[1-(2-Fluoro-4'-bromo-4-biphenylyl)-ethylsulfinyl]-acetic acid methyl ester, was prepared analogous to Example 46 from [1-(2-fluoro-4'-bromo-4-biphenylyl)-ethylthio]-acetic acid methyl ester by oxidation with hydrogen peroxide in glacial acetic acid. Yield of diastereoisomeric mixture: 71% of theory; oil with an $R_f$ value from 0.4 to 0.6. NMR-spectrum (CDCl$_3$): CH$_2$-signals as (a) double doublet at 3.55 ppm (J=15 Hz, $\delta\tau$=32 Hz) and as (b) singlet at 3.35 ppm. One of the isomers was separated as an oil (CH$_2$-signal at 3.55 ppm and $R_f$-value 0.4) by columnchromatography on 50-times its amount of silicagel with cyclohexane/ethyl acetate=½. Yield: 11% of theory; oil with $R_f$-value 0.4 on carrier 1 with cyclohexane/ethyl acetate=¼.

EXAMPLE 56

[1-(2'-Cyano-4-biphenylyl)-ethylsulfinyl]-acetic acid methyl ester, was prepared analogous to Example 46 from [1-(2'-cyano-4-biphenylyl)-ethylthio]-acetic acid methyl ester by oxidation with hydrogen peroxide in glacial acetic acid, followed by purification by column chromatography on silicagel with cyclohexane/ethyl acetate=¼. The diastereoisomeric mixture was an oil with the $R_f$-values 0.3 and 0.4 on carrier 2 with cyclohexane/ethyl acetate=¼.

Analysis: $C_{18}H_{17}NO_3S$; mol. wt. 327.41: Calculated: C—66.03%; H—5.23%; N—4.28%; S—9.79%. Found: C—66.00%; H—5.75%; N—3.63%; S—9.20%.

NMR-spectrum (CDCl$_3$): CH$_2$-signals as (a) double doublet at 3.55 ppm (J=15 Hz) and as (b) singlet at 3.38 ppm. IR-spectrum (CH$_2$Cl$_2$): CN at 2210 cm$^{-1}$, ester-CO at 1730 cm$^{-1}$.

EXAMPLE 57

[1-(4'-Chloro-4-biphenylyl)-ethylsulfinyl]-acetic acid methyl ester, was prepared analogous to Example 34 from the diastereoisomeric mixture of [1-(4'-chloro-4-biphenylyl)-ethylsulfinyl]-acetic acid and methyl iodide in dimethyl sulfoxide in the presence of potassium carbonate. The diastereoisomeric mixture was an oil with the $R_f$-values 0.4 and 0.5 on carrier 2 with cyclohexane/ethyl acetate=¼. Yield: 83% of theory. The two isomers (a) and (b) were separated by column chromatography on 100 times the amount of silicagel with cyclohexane/ethyl acetate=¼.

(a) crystalline oil, $R_f$-value: 0.5 on carrier 2 with cyclohexane/ethyl acetate=¼. Yield: 15% of theory.

Analysis: $C_{17}H_{17}ClO_3S$; mol. wt. 336.79: Calculated: C—60.63%; H—5.09%; Cl—10.53%; S—9.52%. Found: C—60.90%; H—5.33%; Cl—10.23%; S—9.30.

NMR-spectrum (CDCl$_3$): CH$_2$-group as singlet at 3.3 ppm (b) Colorless needles (from isopropanol); m.p. 125°–126° C.; yield: 11.5% of theory.

Analysis: $C_{17}H_{17}ClO_3S$; mol. wt. 336.79: Calculated: C—60.63%; H—5.09%; Cl—10.53%; S—9.52%. Found: C—60.50%; H—5.25%; Cl—10.75%; S—9.70%.

NMR-spectrum (CDCl$_3$): CH$_2$-group as double doublet at 3.45 ppm (J=15 Hz, $\delta\tau$=35 Hz).

$R_f$-value: 0.4 on carrier 2 with cyclohexane/ethyl acetate=¼.

EXAMPLE 58

[1-(2'-Fluoro-4-biphenylyl)-ethylsulfonyl]-acetic acid 170 gm (0.556 mol) of a diastereoisomeric mixture of [1-(2'-fluoro-4-biphenylyl)-ethylsulfinyl]-acetic acid were dissolved in 1.7 liters of acetone, and a solution of 19.9 gm (0.195 mol) of concentrated sulfuric acid inf 70 ml of water was added. While stirring, 67.2 gm (0.425 mol) of potassium permanganate were added in small portions, and the temperature was maintained at 20°–25° C. The mixture was stirred for 1 hour, the manganese dioxide was suction-filtered off, the filter cake was washed with acetone, and the filtrate was evaporated in vacuo. The residue was diluted with 4 liters of glacial acetic acid, and the precipitated crystalline reaction product was suction-filtered off, washed, dried and recrystallized from toluene. Yield: 158.2 gm (88.5% of theory); m.p. 144°–146° C.

Analysis: $C_{16}H_{15}FO_4S$; mol. wt. 322.37: Calculated: C—59.61%; H—4.69%; S—9.95%. Found: C—59.60%; H—4.73%; S—10.10%.

EXAMPLE 59

[1-(2'-Fluoro-4-biphenylyl)-ethylsulfonyl]-acetic acid methyl ester

A solution of 20.0 gm (62 millimoles) of [1-(2'-fluoro-4-biphenylyl)-ethylsulfonyl]-acetic acid in 200 ml of benzene was admixed with 3 gm (79 millimols) of methanol and then with a solution of 15.4 gm (75 millimols) of dicyclohexyl-carbodiimide in 30 ml of benzene. After 1 hour, 100 ml of water and 30 ml of 2 N acetic acid were added, and the mixture was stirred for 15 minutes. Thereafter, the dicyclohexylurea was suction-filtered off, the aqueous phase was separated from the filtrate, and the benzene phase was evaporated. The evaporation residue was recrystallized from toluene/cyclohexane=⅓. Yield: 18.2 gm (88.8% of theory); m.p. 79°–81° C.

Analysis: $C_{17}H_{17}FO_4S$; mol. wt. 336.39: Calculated: C—60.70%; H—5.04%; S—9.53%. Found: C—60.80%; H—5.40%; S—9.55%.

IR-spectrum (methylene chloride): SO$_2$ at 1160 and 1325 cm$^{-1}$, ester CO at 1730 cm$^{-1}$.

EXAMPLE 60

[1-(2'-Fluoro-4-biphenylyl)-ethylsulfonyl]-acetic acid ethyl ester, was prepared analogous to Example 59 from [1-(2'-fluoro-4-biphenylyl)-ethylsulfonyl]-acetic acid by esterification with ethanol in the presence of dicyclohexyl-carbodiimide. Yield: 100% of theory; oil, $R_f$-value: 0.5 on carrier 1 with toluene/ethyl acetate=9/1.

Analysis: $C_{18}H_{19}FO_4S$; mol. wt. 350.42: Calculated: C—61.70%; H—5.47%; S—9.15%. Found: C—61.60%; H—5.63%; S—9.05%.

EXAMPLE 61

[1-(2'-Fluoro-4-biphenylyl)-ethylsulfonyl]-acetic acid n-propyl ester, was prepared analogous to Example 59 from [1-(2'-fluoro-4-biphenylyl)-ethylsulfonyl]-acetic acid by esterification with n-propanol in the presence of dicyclohexyl-carbodiimide. Yield: 100% of theory; oil, $R_f$-value: 0.5 on carrier 1 with toluene/ethyl acetate=9/1.

Analysis: $C_{19}H_{21}FO_4S$; mol. wt. 364.44: Calculated: C—62.62%; H—5.81%; S—8.80%. Found: C—63.70%; H—6.17%; S—8.40%.

EXAMPLE 62

[1-(2'-Fluoro-4-biphenylyl)-ethylsulfonyl]-acetic acid isoamyl ester, was prepared analogous to Example 59 from [1-(2'-fluoro-4-biphenylyl)-ethylsulfonyl]-acetic acid by esterification with isoamyl alcohol in the presence of dicyclohexyl/carbodiimide. Yield: 98% of theory; oil, $R_f$-value: 0.7 on carrier 1 with toluene-ethyl acetate=9/1.

Analysis: $C_{21}H_{25}FO_4S$; mol. wt. 392.49: Calculated: C—64.27%; H—6.42%; S—8.17%. Found: C—65.10%; H—6.71%; S—7.90%.

EXAMPLE 63

[1-(2'-Fluoro-4-biphenylyl)-ethylsulfonyl]-acetic acid n-hexyl ester, was prepared analogous to Example 59 from [1-(2'-fluoro-4-biphenylyl)-ethylsulfonyl]-acetic acid by esterification with n-hexanol in the presence of dicyclohexyl/carbodiimide. Yield: 96% of theory; oil, $R_f$-value: 0.6 on carrier 1 with toluene/ethyl acetate=9/1.

Analysis: $C_{22}H_{27}FO_4S$; mol. wt. 406.51: Calculated: C—65.00%; H—6.69%; S—7.87%. Found: C—65.30%, H—6.86%; S—7.86%.

EXAMPLE 64

[1-(2'-Fluoro-4-biphenylyl)-ethylsulfonyl]-acetic acid benzyl ester, was prepared analogous to Example 59 from [1-(2'-fluoro-4-biphenylyl)-ethylsulfonyl]-acetic acid by esterification with benzyl alcohol in the presence of dicyclohexylcarbodiimide. Yield: 97% of theory; oil, $R_f$-value: 0.6 on carrier 1 with toluene/ethyl acetate=9/1.

Analysis: $C_{23}H_{21}FO_4S$; mol. wt. 412.48: Calculated: C—66.97%; H—5.13%; S—7.77%. Found: C—67.20%; H—5.38%; S—7.55%.

EXAMPLE 65

[1-(2-Fluoro-4'-bromo-4-biphenylyl)-ethylsulfonyl]-acetic acid methyl ester, was prepared analogous to Example 67 from [1-(2-fluoro-4'-bromo-4-biphenylyl)-ethylsulfinyl]-acetic acid methyl ester by oxidation with potassium permanganate in glacial acetic acid. Yield: 95% of theory; oil, $R_f$-value: 0.6 on carrier 1 with cyclohexane/ethyl acetate=1/1.

EXAMPLE 66

[1-(2,2'-Difluoro-4-biphenylyl)-ethylsulfonyl]-acetic acid methyl ester, was prepared analogous to Example 67 from [1-(2,2'-difluoro-4-biphenylyl)-ethylsulfinyl]-acetic acid methyl ester by oxidation with potassium permanaganate in glacial acetic acid. Yield: 97% of theory; oil, $R_f$-value; 0.6 on carrier 1 with cyclohexane/ethyl acetate=1/1.

Analysis: $C_{17}H_{16}F_2O_4S$; mol. wt. 354.38: Calculated: C—57.62%; H—4.55%. Found: C—57.80%; H—5.02%.

EXAMPLE 67

[1-(3'-Chloro-4-biphenylyl)-ethylsulfonyl]-acetic acid and its sodium salt 12.0 gm (37.2 millimols) of [1-3'-chloro-4-biphenylyl)-ethylthio]-acetic acid methyl ester were oxidized in glacial acetic acid with a suspension of 11.8 gm (74.4 millimols) of potassium permanganate in 40 ml of water. The manganese dioxide was destroyed with sodium bisulfite, the mixture was diluted with water and extracted with ethyl acetate. After evaporation of the organic extract, the methyl ester (13.0 gm) obtained as the residue was hydrolyzed with 2.5 gm of sodium hydroxide in 100 ml of methanol into the free acid by boiling for 5 minutes. 10 ml of water were added and the sodium salt was allowed to crystallize out. Yield: 8.5 gm (63% of theory); m.p. 196° C. (decomp.), sintering at 85° C.

Analysis: $C_{16}H_{14}ClNaO_4S$; mol. wt. 360.81 Calculated: C-53.26%; H—3.91%; Cl—9.83%; S—8.89%. Found: C—53.20%; H—4.06%; Cl—9.72%; S—8.74%.

EXAMPLE 68

[1-(4-Biphenylyl)-ethylsulfonyl]-acetic acid, was prepared analogous to Example 67 from [1-(4-biphenylyl)-ethylthio]-acetic acid by oxidation with potassium permanganate. Yield: 88% of theory; m.p. 134°-135° C. (from glacial acetic acid/water=15/35).

Analysis: $C_{16}H_{16}O_4S$; mol. wt. 304.37: Calculated: C—63.14%; H—5.00%; S—10.53%. Found: C—64.00%; H—5.49%; S—10.07%.

EXAMPLE 69

[1-(4-Biphenylyl)-ethylsulfonyl]-acetic acid methyl ester 17.0 gm (56 millimols) of [1-(4-biphenylyl)-ethylsulfonyl]-acetic acid were dissolved in 100 ml of methanol, and 3 ml of phosphorus oxychloride were added to the solution while cooling on ice. The mixture was heated to 35° C. and was then allowed to stand overnight at room temperature. The crystalline reaction product which had separated out was suction-filtered off and recrystallized from 50 ml of isopropanol. Yield: 14.8 gm (83% of theory); m.p. 79°-80° C.

Analysis: $C_{17}H_{18}O_4S$; mol. wt. 418.40: Calculated: C—64.13%; H—5.70%; S—10.07%. Found: C—64.10%; H—5.96%; S—10.28%.

The compounds of the present invention, that is, those embraced by formula I above, their diastereoisomers and optically active antipodes, and their non-toxic salts, have useful pharmacodynamic properties. More particularly, they exhibit an inhibiting effect upon thrombocyte aggregation, a prolonging effect upon the bleeding time, and a lowering effect upon the cholesterol and triglyceride level in the blood in warm-blooded animals, such as cats and mice; therefore, the compounds are useful as antithrombotics, anticoagulants and anti-hypercholesteremics.

The prolonging effect upon the bleeding time and the toxicity of the compound of the instant invention and certain closely related prior art compounds were ascertained by the standard pharmacological test methods described below, and the tables show the results obtained from these test for representative species A–F of the present invention and prior art compounds G–K, where A=Methyl [1-(2'-Fluoro-4-biphenylyl)-ethylsulfinyl]-acetate, m.p. 78°-80° C., B=Methyl [1-(2'-Fluoro-4-biphenylyl)-ethylsulfinyl]-acetate m.p. 92°-94° C., C=Isoamyl [1-(2'-Fluoro-4-biphenylyl)-ethylsulfinyl]-acetate, D=Methyl [3-(4-Biphenylyl)-butyl-(1)-sulfinyl]-acetate, E=Dextrorotatory methyl [1-(2'-fluoro-4-biphenylyl)-ethylsulfinyl]-acetate, F=Levorotatory methyl [1-(2'-fluoro-4-biphenylyl)-ethylsulfinyl]-acetate, G = [4'-Chloro-4-biphenylyl)-methylsulfonyl]-acetic acid (see Example 21 of published Dutch Application No. 67.08766).
H = Methyl 4-Bromo-biphenylyl-4'-sulfinyl-acetate, [see C.A. 66, 37570 (z) 1967].
I = 4-Bromo-biphenylyl-4'-sulfinyl-acetic acid, [see C.A. 66, 37570 (z) 1967].
J = α-[4-(p-Chloro-phenyl)-phenylsulfonyl]-α-methyl-propionic acid, (see British Pat No. 1,121,722) and
K = α-[4-(p-Chloro-phenyl)-phenylsulfinyl]-α-methyl-propionic acid (see British Pat. No. 1,121,722).

1. The prolonging effect upon the bleeding time was ascertained by the method of Duke, J. Amer. Med. Assoc. 15, 1185 (1910). 10 mgm/kg of the test compound were given per os to non-anesthetized mice. One or three hours after administration of the test compound, about 0.5 mm was cut off from the tail of each animal, and the exuded blood was carefully soaked up with filter paper at intervals of 30 seconds. The number of drops of blood so obtained was used as a measure for the bleeding time compared to untreated animals (5 animals/test). The following table shows the results obtained.

TABLE I

| Compound | Prolongation of bleeding time in % after | |
|---|---|---|
| | 1 hour | 3 hours |
| Invention: | | |
| A | 136 | 66 |
| B | 142 | 56 |
| C | 112 | 49 |
| D | 188 | 85 |
| E | 117 | — |
| F | 129 | — |
| Prior art: | | |
| G | 3 | — |
| H | 10 | — |
| I | 10 | — |
| J | 20 | — |
| K | 20 | — |

2. Acute toxicity:

The acute toxicity of the test compounds was determined in white mice (observation time: 14 days) after oral administration of a single dose.

TABLE II

| Compound | acute toxicity |
|---|---|
| Invention: | |
| A | >2000 mgm/kg (1 out of 10 animals died) |
| B | >500 mgm/kg (0 out of 5 animals died) |
| C | >250 mgm/kg (1 out of 5 animals died) |
| D | >250 mgm/kg (0 out of 5 animals died) |
| E | >250 mgm/kg (0 out of 5 animals died) |
| F | >250 mgm/kg (3 out of 10 animals died) |
| Prior art: | |
| G | ~500 mgm/kg (5 out of 10 animals died) |
| H | ~500 mgm/kg (5 out of 10 animals died) |
| I | ~500 mgm/kg (6 out of 10 animals died) |
| J | >1000 mgm/kg (0 out of 10 animals died) |
| K | ~1000 mgm/kg (6 out of 10 animals died) |

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions suspensions, emulsions, syrups, suppositories and the like. One effective antithrombotic, anticoagulant or anti- cholesteremic dosage unit of the compounds acacording to the present invention is from 0.083 to 1.67 mgm/kg body weight, preferably 0.16 to 0.84 mgm/kg body weight. The daily dose rate is from 1.66 to 3.34 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 70

Tablets

The tablet composition is compounded from the following ingredients:

| | |
|---|---|
| [1-(2'-Fluoro-4-biphenylyl)-ethylsulfinyl]-acetic acid methyl ester | 30.0 parts |
| Lactose | 38.0 parts |
| Potato starch | 26.0 parts |
| Polyvinylpyrrolidone | 5.0 parts |
| Magnesium stearate | 1.0 parts |
| Total | 100.0 parts |

Preparation:

The biphenylyl derivative is intimately admixed with the lactose and the potato starch, the mixture is uniformly moistened with an ethanolic 20% solution of the polyvinylpyrrolidone, the moist mass is forced through a 1.5 mm-mesh screen, and the resulting granulate is dried at 45° C. and again passed through a 1.0 mm-mesh screen. The dry granulate thus obtained is admixed with the magnesium stearate, and the composition is compressed into 100 mgm-tablets in a conventional tablet making machine. Each tablet is an oral dosage unit composition containing 30 mgm of the biphenylyl derivative.

EXAMPLE 71

Coated Pills

The pill core composition is compounded from the following ingredients:

| | |
|---|---|
| [1-(2'-Fluoro-4-biphenylyl)-ethylsulfinyl]-acetic acid methyl ester | 15.0 parts |
| Lactose | 14.0 parts |
| Corn starch | 8.0 parts |
| Polyvinylpyrrolidone | 2.5 parts |
| Magnesium stearate | 0.5 parts |
| Total | 40.0 parts |

Preparation:

The ingredients are compounded in a manner analogous to that described in the preceding example, and the composition is compressed into 40 mgm-pill cores, which are subsequently coated with a thin shell consisting essentially of a mixture of talcum and sugar and finally polished with beeswax. Each coated pill is an oral dosage unit composition containing 15 mgm of the biphenylyl derivative.

EXAMPLE 72

Hypodermic Solution

The solution is compounded from the following ingredients:

| [1-(2'-Fluoro-4-biphenylyl)-ethylsulfinyl] | |
|---|---|
| -acetic acid methyl ester | 10.0 parts |
| Polyethyleneglycol 600 | 100.0 parts |
| Distilled water q.s.ad | 2000.0 parts by vol |

Preparation:

The polyethyleneglycol and the biphenylyl derivative are dissolved in a sufficient amount of distilled water which had previously been boiled and cooled in an atmosphere of nitrogen; the dissolution is also carried out in an atmosphere of nitrogen. The resulting solution is diluted to the indicated volume with additional pre-treated distilled water, and the resulting solution is filled, again in an atmosphere of nitrogen, into brown 2 cc-ampules which are then sealed and sterilized for 20 minutes at 120° C. The entire operation must be performed in diffused light. The contents of each ampule are an injectable dosage unit composition containing 10 mgm of the biphenylyl derivative.

EXAMPLE 73

Drop Solution

The solution is compounded from the following ingredients:

| [1-(2'-Fluoro-4-biphenylyl)-ethylsulfinyl] | |
|---|---|
| -acetic acid methyl ester | 10.0 parts |
| Cane sugar | 350.0 parts |
| Essence of cocoa | 50.0 parts |
| Sorbic acid | 1.0 parts |
| Ethyl alcohol | 200.0 parts by vol. |
| Polyethyleneglycol 600 | 100.0 parts by vol. |
| Distilled water q.s.ad | 1000.0 parts by vol. |

Preparation:

The sorbic acid is dissolved in the ethanol, the solution is diluted with an equal volume of distilled water, and the biphenylyl derivative is dissolved in the aqueous mixture (solution 1). The cane sugar is dissolved in the remaining amount of distilled water (solution 2). Solution 2, the polyethyleneglycol and the essence of cocoa are stirred into solution 1, and the composition is filtered. The entire operation must be performed in an atmosphere of nitrogen and in diffused light. 1 ml of the filtrate (about 20 drops) is an oral dosage unit composition containing 10 mgm fo the biphenylyl derivative.

Any one of the other biphenylyl derivatives of the present invention may be substituted for the particular biphenylyl derivative in Examples 70 through 73. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A diastereoisomer or optically active antipode of a compound of the formula

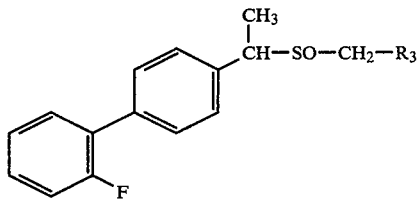

wherein R₃ is (alkoxy of 1 to 6 carbon atoms)-carbonyl.

2. A compound of claim 1, which is methyl [1-(2'-fluoro-4-biphenylyl)-ethylsulfinyl]-acetate, a diastereoisomer thereof or an optically active antipode thereof.

3. A compound of claim 1, which is isoamyl [1-(2'-fluoro-4-biphenylyl)-ethylsulfinyl]-acetate, a diastereoisomer thereof or an optically active antipode thereof.

4. An antithrombotic pharmaceutical composition consisting essentially of an inert pharmaceutical carrier and an effective antithrombotic amount of a compound of claim 1.

5. The method of preventing or alleviating thrombosis in a warm-blooded animal in need of such treatment, which comprises administering to said animal an effective antithrombotic amount of a compound of claim 1.

* * * * *

UNITED STATES PATENT AND TRADEMARK OFFICE
CERTIFICATE OF CORRECTION

PATENT NO. : 4,191,776
DATED : March 4, 1980
INVENTOR(S) : JOSEF NICKL ET AL.

It is certified that error appears in the above-identified patent and that said Letters Patent are hereby corrected as shown below:

Column 2, line 65:   "methoxye" should read -- methoxy --;

line 66:   "thanol" should read -- ethanol --.

Column 7, line 45:   "difficulty" should read -- difficultly --;

line 67:   "e-" should be canceled;

line 68:   "thanol" should read -- ethanol --.

Column 8, line 12:   Before "gm" insert -- 12.9 --

Column 18, line 36:  "A=81-(2'-" should read -- A=[1-(2'- --.

Column 22, line 27:  "millimoles" should read -- millimols --.

Column 25, Table I:  "I  10" should read -- I  5 --.

Signed and Sealed this

Twenty-fourth Day of June 1980

[SEAL]

Attest:

SIDNEY A. DIAMOND

Attesting Officer    Commissioner of Patents and Trademarks